US010408839B2

(12) United States Patent
Brenner et al.

(10) Patent No.: US 10,408,839 B2
(45) Date of Patent: Sep. 10, 2019

(54) BIOMARKER PANEL FOR DIAGNOSING CANCER (71) Applicant: Deutsches Krebsforschungszentrum Stiftung des Öffentlichen Rechts, Heidelberg (DE)

(72) Inventors: Hermann Brenner, Wiesenbach (DE); Hongda Chen, Mannheim (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 0 days.

(21) Appl. No.: 15/561,755

(22) PCT Filed: Mar. 23, 2016

(86) PCT No.: PCT/EP2016/056314
§ 371 (c)(1),
(2) Date: Sep. 26, 2017

(87) PCT Pub. No.: WO2016/156128
PCT Pub. Date: Oct. 6, 2016

(65) Prior Publication Data
US 2018/0080937 A1 Mar. 22, 2018

(30) Foreign Application Priority Data
Mar. 27, 2015 (EP) .................................... 15161465

(51) Int. Cl.
G01N 33/53 (2006.01)
G01N 33/574 (2006.01)
(52) U.S. Cl.
CPC . G01N 33/57488 (2013.01); G01N 33/57419 (2013.01); G01N 33/57438 (2013.01); G01N 33/57446 (2013.01); G01N 2333/485 (2013.01); G01N 2333/495 (2013.01); G01N 2333/521 (2013.01); G01N 2333/525 (2013.01); G01N 2333/5412 (2013.01); G01N 2333/57 (2013.01); G01N 2333/70596 (2013.01); G01N 2333/71 (2013.01); G01N 2333/912 (2013.01); G01N 2333/95 (2013.01); G01N 2800/52 (2013.01); G01N 2800/60 (2013.01); G01N 2800/7028 (2013.01)
(58) Field of Classification Search
None
See application file for complete search history.

(56) References Cited
U.S. PATENT DOCUMENTS

2009/0215053 A1* 8/2009 Galon .............. G01N 33/57484
435/6.16
2009/0275057 A1 11/2009 Linke et al.
2014/0038844 A1* 2/2014 Borrebaeck ...... G01N 33/57438
506/9
2014/0236166 A1 8/2014 Park et al.
2015/0038365 A1* 2/2015 Aghvanyan ...... G01N 33/57423
506/9

FOREIGN PATENT DOCUMENTS

| WO | WO 2004/065583 A2 | 8/2004 |
| WO | WO 2007/025044 A2 | 3/2007 |
| WO | WO 2008/138522 A1 | 11/2008 |
| WO | WO 2012/120288 A2 | 9/2012 |
| WO | WO 2013/152989 A2 | 10/2013 |
| WO | WO 2014/009535 A2 | 1/2014 |
| WO | WO 2014/068124 A1 | 5/2014 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Fitori et al., PKC412 Small-Molecule Tyrosine Kinase Inhibitor, Cancer, Oct. 2007, vol. 110, No. 7, pp. 1457-1468. (Year: 2007).*
International Preliminary Report on Patentability, International Application No. PCT/EP2016/056314, entitled: "Biomarker Panel for Diagnosing Cancer," dated Oct. 3, 2017, 14 pgs.
R. Altena et al., "Growth Differentiation Factor 15 (GDF-15) Plasma Levels Increase during Bleomycin- and Cisplatin-Based Treatment of Testicular Cancer Patients and Relate to Endothelial Damage", PLOS ONE, 10(1):e0115372 (pp. 1-15) (Jan. 15, 2015).
S. M. Cushman et al., "Gene Expression Markers of Efficacy and Resistance to Cetuximab Treatment in Metastatic Colorectal Cancer: Results from CALGB 80203 (Alliance)", Clinical Cancer Research, 21(5):1078-1086 (Published Online Dec. 17, 2014).
S. M. Cushman et al., "Supplementary Tables to Gene Expression Markers of Efficacy and Resistance to Cetuximab Treatment in Metastatic Colorectal Cancer: Results from CALGB 80203 (Alliance)", Clinical Cancer Research, 21(5):1078-1086 (Mar. 1, 2015).
S. M. Cushman et al., "Supplementary Tables to Gene Expression Markers of Efficacy and Resistance to Cetuximab Treatment in Metastatic Colorectal Cancer: Results from CALGB 80203 (Alliance)", Clinical Cancer Research, 21(5):1078-1086 (Mar. 1, 2015) pp. 1-6, XPO55214319, Retrieved from Internet: URL:http://clincancerres.aacrjournals.org/content/21/5/1078/suppl/DC1 [retrieved on Sep. 18, 2015].
Notification of Transmittal of the International Search Report and the Written Opinion of the International Searching Authority, International Application No. PCT/EP2016/056314, entitled "Biomarker Panel for Diagnosing Cancer" dated Aug. 22, 2016 (24 pages).

(Continued)

Primary Examiner — Gary Counts
(74) Attorney, Agent, or Firm — Saul Ewing Arnstein & Lehr LLP; Marry K. Murray (57) ABSTRACT An in vitro method for the diagnosis, prognosis, stratification and/or monitoring of colorectal cancer in a subject includes detecting the level of AREG, CEA, HGF-receptor, ErbB4-Her4, CD69, PSA, EMMPRIN, and INF-gamma biomarkers in a biological sample of the subject. In an embodiment, the subject is administered a treatment when a differential level of the biomarkers compared to a healthy control or a reference value is indicative for the presence of colorectal cancer in the subject.

5 Claims, 4 Drawing Sheets

(56) References Cited

OTHER PUBLICATIONS

T. Ohchi et al., "Amphiregulin Is a Prognostic Factor in Colorectal Cancer", *Anticancer Res.*, 32(6):2315-2321 (2012).
J. R. Sierra et al., "c-MET as a Potential Therapeutic Target and Biomarker in Cancer", *Therapeutic Advances in Medical Oncology*, 3(1): S21-S35 (2011).
Qin Xu et al., "ADAM17 is Associated With EMMPRIN and Predicts Poor Prognosis in Patients with Uterine Cervical Carcinoma", *Tumor Biology*, 35(8): 7575-7586 (2014).

\* cited by examiner

BIOMARKER PANEL FOR DIAGNOSING CANCER

RELATED APPLICATIONS

This application is the U.S. National Stage of International Application No. PCT/EP2016/056314, filed Mar. 23, 2016, which designates the U.S., published in English, and claims priority under 35 U.S.C. §§ 119 or 365(c) to European Application No. 15161465.8, filed on Mar. 27, 2015. The entire teachings of the above application are incorporated herein by reference.

FIELD OF THE INVENTION

The present invention pertains to a new method for the diagnosis, prognosis, stratification and/or monitoring of a therapy, of cancer in a patient. The method is based on the determination of the level of a panel of biomarkers selected from CEA, AREG, IL-6, GDF-15, HGF-receptor, CXCL9, ErbB4-Her4, CXCL10, Flt3L, VEGFR-2, CD69, CXCL5, PSA, EMMPRIN, Cathepsin-D, Caspase-3, TNF-alpha, and INF-gamma. The new biomarker panel of the invention allows diagnosing and even stratifying various cancer diseases. Furthermore provided are diagnostic kits for performing the non-invasive methods of the invention.

DESCRIPTION

A major step in many aspects of research related to diseases such as cancer is the identification of specific and sensitive biomarkers suitable for the development of effective and improved diagnostic, prognostic and therapeutic modalities. An aim of the present invention is to provide novel biomarkers and biomarker panels for use as novel diagnostic and/or prognostic markers and/or for use in the development of novel therapeutics. Whilst mass spectrometry, shot gun proteomics and DNA/RNA microarray analyses, and deep sequencing have resulted in an increasing list of reported potential tumor biomarkers, very few have found their way into the clinical validation phase and even fewer are used as reliable therapeutic targets or diagnostic markers.

With more than 1.2 million new colorectal cancer (CRC) cases and 600,000 deaths occurring every year, CRC is the third most commonly diagnosed cancer and the fourth most common cancer cause of death worldwide. Due to the slow progression from precancerous lesions to CRC, early detection could strongly reduce the burden of this disease. However, sigmoidoscopy and colonoscopy, the current gold standards for detection of CRC in the distal and total colorectum, respectively, are limited by several disadvantages, such as high costs, limited resources and low compliance. Established non-invasive screening tests are based on stool testing, such as guaiac based faecal occult blood tests (gFOBTs) and faecal immunochemical tests (FITs). However, gFOBTs are limited by low sensitivity and both gFOBTs and FITs face limitations in adherence related to the need of stool collection.

Due to their non-invasive nature and ease of application in routine medical practice, blood-based tests could ensure high levels of adherence when applied as primary screening tools in population-based CRC screening, especially for individuals who don't prefer stool sampling, and search for blood-based screening tests is a very active research area. However, most previous studies aiming to discover and validate novel blood-based screening markers recruited participants directly from hospitals. In such clinical settings, the CRC cases typically include a higher proportion of cases in advanced tumor stage than in screening settings. Furthermore, cases may have undertaken some diagnostic or early therapeutic procedures, which may influence potential biomarkers and might lead to overestimation of differences from biomarker levels in healthy controls and hence of diagnostic performance. Additionally, confounding may result from non-comparability of cases and controls with respect to other factors, such as other medical conditions, setting of recruitment, or pre-analytical handling of blood samples. Therefore, it is a critical issue to identify biomarkers and to evaluate their diagnostic performance in a true screening setting.

Even though different blood biomarkers, such as Septin 9 have been evaluated in both clinical and screening settings, direct comparative analyses of a large number of biomarkers in the same study are still sparse, which makes reported differences in diagnostic performance from different studies difficult to interpret and therefore calls for head-to-head comparisons of a large number of biomarkers in the same study. Novel laboratory techniques allow for such evaluation as well as for evaluation of combinations of the most promising markers, but a very critical issue in the evaluation of such high-dimensional data is rigorous adjustment for potential overoptimism resulting from overfitting.

Due to the continuing need for quick, but sensitive and specific cancer diagnostics the present invention seeks to provide a novel approach for a simple and minimal invasive but specific and sensitive test system for the diagnosis or monitoring various cancer diseases.

The above problem is solved in a first aspect by a non-invasive method for the diagnosis, prognosis, stratification and/or monitoring of a therapy, of a cancer disease in a subject, comprising the steps of:
 (a) Providing a biological sample from the subject,
 (b) Determining the level of one or more biomarkers selected from the group consisting of CEA, AREG, IL-6, GDF-15, HGF-receptor, CXCL9, ErbB4-Her4, CXCL10, Flt3L, VEGFR-2, CD69, CXCL5, PSA, EMMPRIN, Cathepsin-D, Caspase-3, TNF-alpha, and INF-gamma, in the biological sample,
wherein a differential level of one or more of the biomarkers in the biological sample from the subject as determined in step (b) compared to a healthy control or reference value is indicative for the presence of a cancer disease in the subject.

A "diagnosis" or the term "diagnostic" in context of the present invention means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The term "prognosis" refers to a forecast as to the probable outcome of the disease as well as the prospect of recovery from the disease as indicated by the nature and symptoms of the case. Accordingly, a negative or poor prognosis is defined by a lower post-treatment survival term or survival rate. Conversely, a positive or good prognosis is defined by an elevated post-treatment survival term or survival rate. Usually prognosis is provided as the time of progression free survival or overall survival.

The term "stratification" for the purposes of this invention refers to the advantage that the method according to the invention renders possible decisions for the treatment and therapy of the patient, whether it is the hospitalization of the patient, the use, effect and/or dosage of one or more drugs, a therapeutic measure or the monitoring of a course of the disease and the course of therapy or etiology or classification of a disease, e.g., into a new or existing subtype or the differentiation of diseases and the patients thereof. Particularly with regard to colorectal cancer, "stratification" means in this context a classification of a colorectal cancer as early or late stage colorectal cancer.

The term "monitoring a therapy" means for the purpose of the present invention to observe disease progression in a subject who receives a cancer therapy. In other words, the subject during the therapy is regularly monitored for the effect of the applied therapy, which allows the medical practitioner to estimate at an early stage during the therapy whether the prescribed treatment is effective or not, and therefore to adjust the treatment regime accordingly.

As used herein, the term "subject" or "patient" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject. As used herein, the term "subject suspected of having cancer" refers to a subject that presents one or more symptoms indicative of a cancer (e.g., a noticeable lump or mass). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the subtype or stage of cancer is not known. The term further includes people who once had cancer (e.g., an individual in remission), and people who have cancer and are suspected to have a metastatic spread of the primary tumor. In this regard the present invention is also applicable as follow-up care for monitoring a subject for a reoccurrence of the cancer.

The term "cancer" and "cancer cells" refers to any cells that exhibit uncontrolled growth in a tissue or organ of a multicellular organism. Particular preferred cancers in context of the present invention are selected from colorectal cancer, pancreatic cancer, gastric cancer, breast cancer, lung cancer, prostate cancer, hepatocellular cancer, cervical cancer, ovarian cancer, liver cancer, bladder cancer, cancer of the urinary tract, thyroid cancer, renal cancer, carcinoma, melanoma, leukemia or brain cancer.

As used herein, the term "colorectal cancer" includes the well-accepted medical definition that defines colorectal cancer as a medical condition characterized by cancer of cells of the intestinal tract below the small intestine (i.e., the large intestine (colon), including the cecum, ascending colon, transverse colon, descending colon, sigmoid colon, and rectum). Additionally, as used herein, the term "colorectal cancer" also further includes medical conditions, which are characterized by cancer of cells of the duodenum and small intestine (jejunum and ileum).

As used herein, the terms "gastric cancer" or "stomach cancer" refer to cancers of the stomach. The most common types of gastric cancer are carcinomas, such as but not limited to, adenocarcinomas, affecting the epithelial cells of the stomach. Stomach cancers may additionally include, for example, sarcomas affecting the connective tissue of the stomach and blastomas affecting the blast tissue of the stomach.

The term "pancreatic cancer" encompasses benign or malignant forms of pancreatic cancer, as well as any particular type of cancer arising from cells of the pancreas (e.g., duct cell carcinoma, acinar cell carcinoma, papillary carcinoma, adenosquamous carcinoma, undifferentiated carcinoma, mucinous carcinoma, giant cell carcinoma, mixed type pancreatic cancer, small cell carcinoma, cystadenocarcinoma, unclassified pancreatic cancers, pancreatoblastoma, and papillary-cystic neoplasm, and the like.).

The term "biological sample" as used herein refers to a sample that was obtained and may be assayed for any one of the biomarkers as disclosed with the present invention, or their gene expression. The biological sample can include a biological fluid (e.g., blood, cerebrospinal fluid, urine, plasma, serum), tissue biopsy, and the like. In some embodiments, the sample is a tissue sample, for example, tumor tissue, and may be fresh, frozen, or archival paraffin embedded tissue. Preferred samples for the purposes of the present invention are bodily fluids, in particular blood or plasma samples.

A "biomarker" or "marker" in the context of the present invention refers to an organic biomolecule, particularly a polypeptide, which is differentially present in a sample taken from subjects having a certain condition as compared to a comparable sample taken from subjects who do not have said condition (e.g., negative diagnosis, normal or healthy subject, or non-cancer patients, depending on whether the patient is tested for cancer, or metastatic cancer). For examples, a marker can be a polypeptide or polysaccharide (having a particular apparent molecular weight) which is present at an elevated or decreased level in samples of cancer patients compared to samples of patients with a negative diagnosis.

The term "determining the level of" a biomarker in a sample, control or reference, as described herein shall refer to the quantification of the presence of said biomarkers in the testes sample. For example the concentration of the biomarkers in said samples may be directly quantified via measuring the amount of protein/polypeptide/polysaccharide as present in the tested sample. However, also possible is to quantify the amount of biomarker indirectly via assessing the gene expression of the encoding gene of the biomarker, for example by quantification of the expressed mRNA encoding for the respective biomarker. The present invention shall not be restricted to any particular method for determining the level of a given biomarker, but shall encompass all means that allow for a quantification, or estimation, of the level of said biomarker, either directly or indirectly. "Level" in the context of the present invention is therefore a parameter describing the absolute amount of a biomarker in a given sample, for example as absolute weight, volume, or molar amounts; or alternatively "level" pertains to the relative amounts, for example and preferably the concentration of said biomarker in the tested sample, for example mol/l, g/l, g/mol etc. In preferred embodiments the "level" refers to the concentration of the tested biomarkers in g/l.

"Increase" of the level of a biomarker in a sample compared to a control shall in preferred embodiments refer to statistically significant increase in preferred aspects of the invention.

In alternative embodiments of the invention, certain biomarkers as disclosed herein may also be significantly decreased in the event of a cancer disease in a subject.

In course of the present invention plasma levels of 92 tumor-associated proteins were measured in all available 35 carriers of colorectal cancer (CRC) and a representative sample of 54 controls free of neoplasm recruited from 5516 participants of screening colonoscopy in 2005-2012. The inventors aimed for a head-to head comparison of the diagnostic performance of these 92 biomarkers and to derive and validate an algorithm based on a combination of the most promising markers for early detection of CRC, paying particular attention to rigorous adjustment for potential overestimation of diagnostic performance. Results were further validated in an independent sample of 54 CRC cases and 38 controls, as well as in other cancer diseases such as gastric cancer or pancreatic cancer.

In a preferred embodiment the method of the herein disclosed invention is performed in vitro or ex vivo. Since the herein described diagnostic methods are non-invasive the term "providing a biological" sample shall preferably not be interpreted to include a surgical procedure conducted at the subject.

Preferred embodiments of the present invention pertain to panels of a plurality of biomarkers as identified herein for the diagnostic purposes as described. The advantage of combing the biomarkers disclosed herein is an increased sensitivity and/or specificity of the disclosed assays. Hence a preferred embodiment of the invention pertains to the herein disclosed method wherein step (b) comprises determining the level of at least two, three, four, five, six, seven or eight biomarkers in the biological sample. Most preferred is that at least four biomarkers are used. More preferred is that at least 5 biomarkers are used. More preferred is that at least 6 biomarkers are used. More preferred is that at least 7 biomarkers are used. Most preferred is that at least 8 biomarkers are used.

In one embodiment of the herein disclosed invention the level of at least CEA, AREG, and GDF-15, in the biological sample, is determined. In addition one of the following biomarkers may be, if desired, be added to the panel for testing: IL-6, INF-gamma, EMMPRIN, ErbB4-Her4, PSA, CD69, and, HGF-receptor.

One specifically preferred panel for use in context of the herein disclosed invention comprises the selected of at least 4, 5, 6, 7 or 8 biomarkers selected from the group of INF-gamma, EMMPRIN, ErbB4-Her4, PSA, CD69, AREG, HGF-receptor and CEA, in the biological sample. Most preferred in this aspect is that at least the biomarkers CEA and AREG, optionally any of the remaining biomarkers is included in this panel. The most preferred embodiment of the invention however relates to the application of a panel of all 8 biomarkers, optionally wherein 1 or 2 biomarkers are substituted with others, or omitted. The complete set of all 8 preferred biomarkers is however the most preferred panel of the invention.

In this regard it is preferred that the analysis of the marker panel in step (b) of the diagnostic method of the invention is characterized in that the tested marker panel has an apparent area under the curve (AUC) at 95% confidence interval (CI) of at least 60%, preferably at least 65% or more preferably at least 70%. How to determine the AUC is known to the skilled artisan. Alternatively or additionally the panel of the invention may be characterized by a sensitivity of at least 75%, preferably at least 80%, and a specificity of at least 40%, preferably at least 50%, more preferably at least 60%.

To date, no single blood biomarker qualifying for mass screening has been identified. The combination of multiple markers might be a more promising approach to achieve the necessary sensitivity and specificity for application in mass screening. Although other marker panels were tested in the prior art, the apparent differences to the panel as provided herein can be explained by the fact that those prior art studies were done in a clinical setting and did not apply any adjustment for over-optimism (not doing so would have yielded an even higher AUC in our study). The above mentioned limitations were also shared by many other studies regarding blood biomarkers for CRC detection. For reasons outlined in detail in the introduction, it is a critical issue to identify for and evaluate biomarkers in samples from screening settings in order to obtain valid performance characteristics under screening conditions. Furthermore, as demonstrated herein, correction for overfitting (cross-validation, bootstrap techniques) and/or external validation are also indispensable to adjust for potential overestimation of diagnostic performance. Hence, the marker panel of the present invention is advantageous over previous prior art panels.

The biomarkers of the invention are preferably protein biomarkers.

The biomarker panel as disclosed herein is particular useful in a cancer screening setting. Cancer screening in the herein disclosed invention shall refer to a procedure where a subject is for which not diagnosis was established is tested for the presence of the cancer disease. This shall not be interpreted to exclude the use of the biomarker of the invention for a diagnostic of a subject that was already diagnosed to suffer from a cancer disease. Non limiting examples for such an application are confirmation of a diagnosis, monitoring or treatment success or monitoring reoccurrence of a cancer in a subject that already received a treatment and wherein cancer is in remission or was cured.

In context of the herein disclosed invention several biomarkers where found to be either differentially up regulated or down regulated in a cancer diagnosis compared to healthy subjects (see table 2). Hence in context of the herein disclosed invention a differential level of a biomarker selected from CEA, GDF-15, AREG, IL-6, CXCL10, CXCL9, PSA, TNF-alpha, and Cathepsin-D, is a higher level of that biomarker in a positive diagnosis. On the other hand, a differential level of a biomarker selected from HGF-receptor, ErbB4-Her4, CXCL5, Flt3L, EMMPRIN, VEGFR-2, CD69 and Caspase-3, is a lower level, in a positive diagnosis.

The skilled artisan will understand that numerous methods may be used to select a threshold or reference value for a particular marker or a plurality of markers. In diagnostic aspects, a threshold value may be obtained by performing the assay method on samples obtained from a population of patients having a certain type of cancer, and from a second population of subjects that do not have cancer. For prognostic or treatment monitoring applications, a population of patients, all of which have, for example, ovarian cancer, may be followed for the time period of interest (e.g., six months following diagnosis or treatment, respectively), and then dividing the population into two groups: a first group of subjects that progress to an endpoint (e.g., recurrence of disease, death); and a second group of subjects that did not progress to the end point. These are used to establish "low risk" and "high risk" population values for the marker(s) measured, respectively. Other suitable endpoints include, but are not limited to, 5-year mortality rates or progression to metastatic disease.

Once these groups are established, one or more thresholds may be selected that provide an acceptable ability to predict diagnosis, prognostic risk, treatment success, etc. In practice, Receiver Operating Characteristic curves, or "ROC" curves, are typically calculated by plotting the value of a variable versus its relative frequency in two populations (called arbitrarily "disease" and "normal" or "low risk" and "high risk" for example). For any particular marker, a distribution of marker levels for subjects with and without a disease may overlap. Under such conditions, a test does not absolutely distinguish "disease" and "normal" with 100% accuracy, and the area of overlap indicates where the test cannot distinguish "disease" and "normal." A threshold is selected, above which (or below which, depending on how a marker changes with the disease) the test is considered to be "positive" and below which the test is considered to be "negative." The area under the ROC curve (AUC) is a measure of the probability that the perceived measurement may allow correct identification of a condition.

Additionally, thresholds may be established by obtaining an earlier marker result from the same patient, to which later results may be compared. In some aspects, the individuals act as their own "control group." In markers that increase with disease severity or prognostic risk, an increase over time in the same patient can indicate a worsening of disease or a failure of a treatment regimen, while a decrease over time can indicate remission of disease or success of a treatment regimen.

In some embodiments, multiple thresholds or reference values may be determined. This can be the case in so-called "tertile," "quartile," or "quintile" analyses. In these methods, the "disease" and "normal" groups (or "low risk" and "high risk") groups can be considered together as a single population, and are divided into 3, 4, or 5 (or more) "bins" having equal numbers of individuals. The boundary between two of these "bins" may be considered "thresholds." A risk (of a particular diagnosis or prognosis for example) can be assigned based on which "bin" a test subject falls into.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. In particularly preferred embodiments of the invention the term "about" may refer to a deviation of the respective numeric value of a maximum of 20% of the numerical value, however more preferred is 15%, 10%, 5% and most preferred is 4%, 3%, 2%, and most preferred is 1%.

In a preferred embodiment said sample is selected from the group consisting of body fluids or tissue, preferably wherein said body fluid sample is a blood sample, more preferably a plasma or serum sample.

In all aspects and embodiments of the present invention in may be preferred that the level of said at least one biomarker in said sample is determined by means of a nucleic acid detection method or a protein detection method. However, nucleic acid detection methods are only applicable where an expressed protein is the biomarker. Generally all means shall be comprised by the present invention which allow for a quantification of the expression of any one of the herein disclosed biomarker. Therefore also promoter analysis and procedures assessing the epigenetic status of a gene locus encoding a protein biomarker of the invention are comprised by the herein described invention.

Detection methods that are preferred in context of the herein described invention the level of said at least one biomarker in said sample is determined by means of a detection method selected from the group consisting of mass spectrometry, mass spectrometry immunoassay (MSIA), antibody-based protein chips, 2-dimensional gel electrophoresis, stable isotope standard capture with anti-peptide antibodies (SISCAPA), high-performance liquid chromatography (HPLC), western blot, cytometry bead array (CBA), protein immuno-precipitation, radio immunoassay, ligand binding assay, and enzyme-linked immunosorbent assay (ELISA), preferably wherein said protein detection method is ELISA. Suitable alternative detection methods for quantification of a biomarker of the invention are known to the skilled artisan.

In yet another aspect, the invention provides kits for aiding a diagnosis of cancer, wherein the kits can be used to detect the biomarkers of the present invention. For example, the kits can be used to detect any one or combination of biomarkers described above, which biomarkers are differentially present in samples of a patient having the cancer and healthy patients. The kits of the invention have many applications. For example, the kits can be used to differentiate if a subject has the cancer, or has a negative diagnosis, thus aiding a cancer diagnosis. In another example, the kits can be used to identify compounds that modulate expression of the biomarkers in in vitro cancer cells or in vivo animal models for cancer.

Optionally, the kit can further comprise instructions for suitable operational parameters in the form of a label or a separate insert. For example, the kit may have standard instructions informing a consumer how to wash the probe after a sample of plasma is contacted on the probe.

In another embodiment, a kit comprises (a) an antibody that specifically binds to a marker; and (b) a detection reagent. Such kits can be prepared from the materials, and the previous discussion regarding the materials (e.g., antibodies, detection reagents, immobilized supports, etc.) is fully applicable to this section and need not be repeated.

In either embodiment, the kit may optionally further comprise a standard or control information so that the test sample can be compared with the control information standard to determine if the test amount of a marker detected in a sample is a diagnostic amount consistent with a diagnosis of cancer.

Preferably the kit of the invention is a diagnostic kit for performing a method in accordance with the present invention comprising means for quantifying the level of said at least one biomarker. Preferably the kit of the invention comprises means for quantifying a biomarker selected from CEA, AREG, IL-6, GDF-15, HGF-receptor, CXCL9, ErbB4-Her4, CXCL10, Flt3L, VEGFR-2, CD69, CXCL5, PSA, EMMPRIN, Cathepsin-D, Caspase-3, TNF-alpha, and INF-gamma. Such means for quantifying is for example at least one antibody, preferably wherein the antibody is a monoclonal antibody, such as a monoclonal antibody that specifically binds to any of the aforementioned biomarkers. Such antibodies are known in the art and commercially available.

The diagnostic kit of the invention in another embodiment comprises at least 8 antibodies which each specifically bind to INF-gamma, EMMPRIN, ErbB4-Her4, PSA, CD69, AREG, HGF-receptor and CEA, preferably wherein said antibodies are monoclonal antibodies.

The present invention will now be further described in the following examples with reference to the accompanying figures and sequences, nevertheless, without being limited thereto. For the purposes of the present invention, all references as cited herein are incorporated by reference in their entireties. In the Figures and Sequences:

EXAMPLES

Materials and Methods

1. Study Design and Study Population

The analysis was conducted in the context of the BliTz study ("Begleitende Evaluierung innovativer Testverfahren zur Darmkrebsfrüherkennung"). Briefly, BliTz is an ongoing study among participants of screening colonoscopy conducted in cooperation with 20 gastroenterology practices in South-western Germany since November 2005, which aims to evaluate novel promising biomarkers for early detection of CRC. Participants are recruited, and blood samples are taken in the practices at a preparatory visit, typically about one week prior to the screening colonoscopy.

For this analysis, the following exclusion criteria were applied to exclude participants without adequate blood samples, participants who do not represent a true screening setting, and participants with potentially false negative results at screening colonoscopy: blood samples taken after screening colonoscopy or blood samples with unknown date of blood withdrawal, history of CRC or inflammatory bowel disease, previous colonoscopy history in the last five years or unknown colonoscopy history, incomplete colonoscopy or insufficient bowel preparation (latter two criteria only for controls). From the remaining participants of the BliTz study recruited in 2005-2012 (N=4345), all 35 available cases with newly detected CRC were included in the analysis. For comparison, the inventors included a representative sample of 54 controls free of colorectal neoplasms. Because this study was conducted in a true screening population in which patients with CRC are expected to be on average slightly older and to include a somewhat large proportion of men, the inventors did not match for these factors as this might lead to biased estimates of specificity in such a setting.

For an independent validation, the inventors also included 54 additional CRC cases (recruited at four hospitals in and around the city of Heidelberg after diagnosis but before initiation of treatment) and 38 additional randomly selected controls free of neoplasm from the BliTz study.

Colonoscopy and histology reports (BliTz study) and hospital records (54 CRC cases for the independent validation set) were collected from all participants. Relevant information was extracted by two research assistants independently who were blind to the blood test results. Tumor stages were classified according to the UICC TNM classification.

2. Laboratory Procedures
2.1. Sample Preparation

Blood samples from participants giving informed consent were to be collected before bowel preparation for colonoscopy (BliTz study) or prior to large bowel surgery or neoadjuvant chemotherapy (54 CRC cases from the clinical setting) in EDTA tubes. The blood samples were immediately centrifuged at 2123 g for 10 minutes at 4° C. and the supernatant was transferred into new tubes, and transported to the biobank at DKFZ in a cool chain, where plasma samples were stored at −80° C. until analyses.

2.2. Laboratory Measurements

Protein profiling was performed using Proseek Multiplex Oncology $I^{96\times96}$ (Olink Bioscience, Uppsala, Sweden) which enables quantification of 92 human tumor-associated protein biomarkers (full marker list in Supplementary Table S1). The panel of 92 protein biomarkers reflects various biological mechanisms involved in carcinogenesis, such as angiogenesis, cell-cell signaling, growth control and inflammation. All laboratory operations were conducted according to the Proseek Multiplex Oncology $I^{96\times96}$ User Manual in the TATAA Biocenter (Göteborg, Sweden). In short, the Prossek reagents are based on the Proximity Extension Assay (PEA) technology, where 92 oligonucleotide labeled antibody probe pairs are allowed to bind to their respective target present in the sample. A PCR reporter sequence is formed by a proximity dependent DNA polymerization event and is subsequently detected and quantified using real-time PCR. Four internal controls (including two incubation controls, one extension control and one detection control) were included in the assay. In addition, there were three replicates of negative controls which were used to calculate the lower limit of detection (LOD) for each protein. All information regarding the study population was blind to the laboratory operators.

3. Data Normalization and Statistical Analyses
3.1 Data Normalization

Normalization of raw data followed the standard protocol from the manufacturer and was conducted through the Olink Wizard of GenEx software (MultiD, Göteborg, Sweden). For each data point, the raw Cq-value (in $\log_2$ scale) was exported from the Fluidigm Real-Time PCR Analysis Software. The first step of normalization is to subtract the raw Cq-value for the extension control for the corresponding sample in order to correct for technical variation. The calculated Cq-values (dCq-value) were further normalized against the negative control determined in the measurement, which yieded ddCq-values (hereafter: Cq-value, in $\log_2$ scale) and could be used for further analyses. LOD was defined as the mean value of the three negative controls plus 3 calculated standard deviations. Missing data and data with a value lower than LOD were replaced with LOD in the following statistical analyses.

3.2 Statistical Analyses

The plasma protein levels (Cq-value) were first compared between CRC cases and neoplasm-free controls using Wilcoxon Rank Sum Test (hereafter: Wilcoxon test), and Benjamini & Hochberg method was additionally employed for multiple testing. The following diagnosis-related indicators were used for evaluating the diagnostic performance of each protein biomarker: sensitivity (true positive rate), specificity (true negative rate), receiver operating characteristics (ROC) curve, and area under the ROC curve (AUC). For each individual protein biomarker, a logistic regression model was used to construct the prediction model. Based on the predicted possibilities from the prediction model, the AUCs and their 95% confidence intervals (95% CIs, calculated based on 2000 bootstrap samples) were derived. Moreover, sensitivities of each individual biomarker at cutoffs yielding 80% and 90% specificity were calculated. In addition to direct estimates of the diagnosis related indicators, the 0.632+ bootstrap method (1000 bootstrap samples with replacement) was applied to adjust for potential overestimation of diagnostic performance. Furthermore, for the biomarkers which were identified to have significantly different plasma levels between CRC cases and controls, stage-specific AUCs (apparent and 0.632+ adjusted AUCs) were also calculated and Delong test was employed to compare the differences of apparent AUCs between early stages (i.e., tumor stage I/II) and advanced stages (i.e., tumor stage III/IV).

A multi-marker algorithm was derived by applying the Lasso logistic regression model based on all 92 protein markers. With the purpose of adjusting for potential overfitting of the prediction algorithm, a "0.632+ bootstrap subsampling approach" was conducted in the following way: i) generate 1000 bootstrap samples (subsampling method, bootstrap without replacement); ii) for each bootstrap sample set, apply the Lasso logistic regression procedure to select variables and to construct a prediction algorithm; iii) apply this algorithm on those patients not included in the bootstrap sample to obtain bootstrap estimates of prediction errors for each bootstrap sample; iv) further adjust these results using the 0.632+ method to obtain a nearly unbiased estimate of the prognostic AUC of the original algorithm. Construction of the algorithm was done including all CRC cases. Evaluation was likewise performed for all CRC cases and, in addition separately for CRC cases at early and advanced tumor stages. Finally, AUC and sensitivity at cutoffs yielding 80% and 90% specificity, respectively, and their 95% CIs of the multi-marker algorithm were determined in the independent validation sample.

Statistical analyses were performed with the statistical software R version 3.0.3. R package "Daim" was used to conduct 0.632+ bootstrap analyses for single markers R package "glmnet" was employed to perform the Lasso logistic regression analysis for multi-marker analyses. Additionally, R packages "peperr" and "c060" were applied to conduct the "632+ bootstrap subsampling approach" described above. All tests were two-sided and p-values of 0.05 or less were considered to be statistically significant.

Example 1: Identification of 17 Biomarkers

Figure 1:
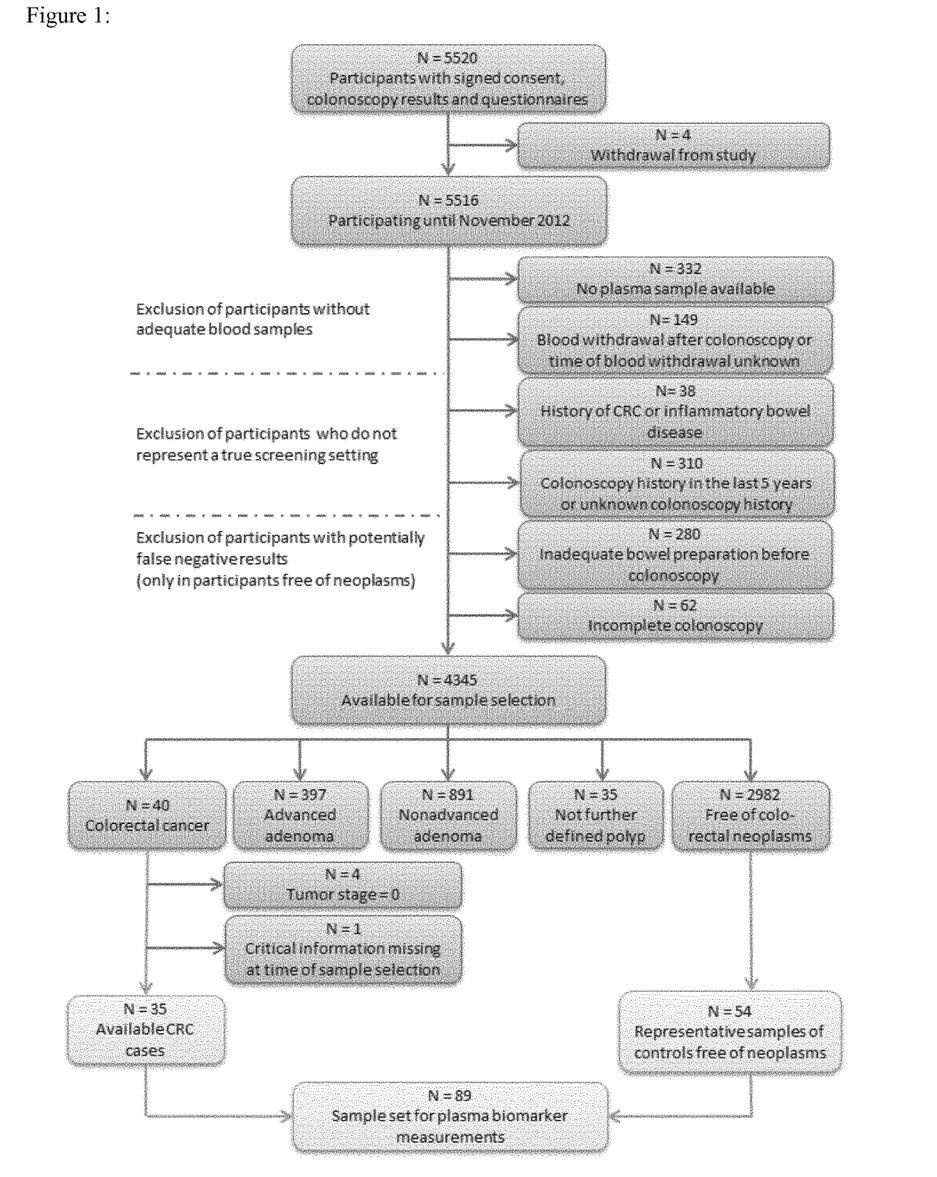
FIG. 1: STAndards for the Reporting of Diagnostic accuracy studies (STARD) diagram of the participants in the BliTz study (2005-2012).

FIG. 1 provides the STAandards for the Reporting of Diagnostic accuracy studies (STARD) diagram which shows the selection of study participants from all subjects enrolled in the BliTz study in 2005-2012. The final study sample included 35 CRC patients who were compared to a representative sample of 54 controls free of colorectal neoplasms. Latter included 6 participants with hyperplastic polyps and 48 participants without colorectal polyps.

Table 1 presents the distribution of socio-demographic characteristics in the CRC case group and the control group. The controls were on average slightly younger than cases (mean±standard deviation: 62.8±7.0 versus 66.9±6.5 years).

TABLE 1

Characteristics of the study population

| Variable | CRC cases (%) | Controls[a] (%) |
|---|---|---|
| Age (years) | | |
| <60 | 5 (14.3) | 24 (44.4) |
| 60-64 | 9 (25.7) | 9 (16.7) |
| 65-69 | 8 (22.9) | 8 (14.8) |
| ≥70 | 13 (37.1) | 13 (24.1) |
| Mean ± SD | 66.9 ± 6.5 | 62.8 ± 7.0 |
| Sex | | |
| Male | 25 (71.4) | 27 (50.0) |
| Female | 10 (28.6) | 27 (50.0) |
| UICC tumor stage | | |
| I | 13 (37.1) | |
| II | 4 (11.4) | |
| III | 16 (45.7) | |
| IV | 2 (5.7) | |
| CRC location | | |
| Colon | 17 (48.6) | |
| Rectum | 17 (48.6) | |
| Unkown | 1 (2.8) | |
| Total | 35 (100.0) | 54 (100.0) |

[a]Controls included 6 participants with hyperplastic polyps and 48 participants without any finding at colonoscopy.

TABLE 2

Diagnostic performance of protein biomarkers showing significant differences between CRC case and controls

| Marker | Median Cq CRC | Median Cq Controls | p-value[a] | Adjusted p-value[b] | Apparent AUC [95% CI] | .632+ AUC [95% CI] | .632+ sens.[c] at 80% spec. | .632+ sens.[c] at 90% spec. |
|---|---|---|---|---|---|---|---|---|
| CEA | 1.20 | 0.49 | <0.001 | 0.015 | 0.73[0.63-0.84] | 0.69[0.57-0.88] | 52% | 27% |
| GDF-15 | 5.34 | 4.68 | <0.001 | 0.016 | 0.72[0.62-0.83] | 0.69[0.58-0.87] | 43% | 18% |
| AREG | 2.73 | 2.41 | 0.001 | 0.016 | 0.72[0.61-0.83] | 0.70[0.57-0.86] | 46% | 36% |
| IL-6 | 4.23 | 3.59 | 0.003 | 0.063 | 0.69[0.58-0.80] | 0.65[0.54-0.84] | 42% | 16% |
| CXCL10 | 6.84 | 6.20 | 0.013 | 0.184 | 0.66[0.54-0.77] | 0.60[0.46-0.80] | 27% | 12% |
| HGF-receptor | 7.25 | 7.32 | 0.013 | 0.184 | 0.66[0.54-0.77] | 0.62[0.48-0.81] | 31% | 18% |
| CXCL9 | 5.78 | 5.23 | 0.014 | 0.184 | 0.66[0.54-0.77] | 0.59[0.45-0.81] | 28% | 13% |
| ErbB4-Her4 | 6.67 | 6.76 | 0.017 | 0.198 | 0.65[0.54-0.77] | 0.60[0.49-0.79] | 32% | 16% |
| CXCL5 | 5.74 | 6.32 | 0.030 | 0.244 | 0.64[0.52-0.76] | 0.59[0.44-0.79] | 35% | 22% |
| Flt3L | 6.95 | 7.17 | 0.030 | 0.244 | 0.64[0.52-0.75] | 0.59[0.48-0.78] | 30% | 14% |
| EMMPRIN | 7.09 | 7.19 | 0.033 | 0.244 | 0.63[0.52-0.75] | 0.59[0.46-0.79] | 28% | 13% |
| PSA | 2.24 | 1.20 | 0.041 | 0.244 | 0.63[0.50-0.75] | 0.59[0.44-0.79] | 33% | 18% |
| TNF-alpha | −0.52 | −0.78 | 0.042 | 0.244 | 0.63[0.51-0.75] | 0.57[0.44-0.79] | 27% | 18% |
| VEGFR-2 | 2.57 | 2.70 | 0.043 | 0.244 | 0.63[0.51-0.75] | 0.58[0.43-0.78] | 30% | 17% |
| CD69 | 6.67 | 7.19 | 0.044 | 0.244 | 0.63[0.51-0.75] | 0.59[0.45-0.79] | 29% | 16% |
| Cathepsin-D | 2.48 | 2.31 | 0.045 | 0.244 | 0.63[0.51-0.74] | 0.55[0.34-0.77] | 25% | 12% |
| Caspase-3 | 10.28 | 10.70 | 0.045 | 0.244 | 0.63[0.51-0.75] | 0.57[0.43-0.78] | 28% | 15% |

[a]Wilcoxon Rank Sum Test to compare the protein expression differences between CRC cases and controls.
[b]The p-value was adjusted for multiple testing by Benjamini & Hochberg method.
[c]Sensitivities were adjusted by using the .632+ bootstrap method.
Abbreviations: AUC, area under the receiver operating characteristic curve; CI, confidence interval.

71.4% of the patients with CRC were men, compared with 50.0% of those free of colorectal neoplasms. Approximately equal proportions of patients were diagnosed in early (stage I/II) and advanced stage (stage III/IV), and there were equal numbers of patients with colon and rectum cancer.

Overall, there were 17 protein biomarkers showing significantly different plasma levels between CRC cases and controls (Table 2). When using 25% false positive rate (FDR) as the cutoff level for multiple testing, all the 17 biomarkers were still statistically significant.

Carcinoembryonic antigen (CEA), growth differentiation factor 15 (GDF-15) and amphiregulin (AREG) met a FDR threshold of 5%. Apart from prostate specific antigen (PSA), for which statistically significantly higher plasma levels in men than in women were found, all the other 16 biomarkers did not show any statistically significant relationship with sex or age within the group of controls free of colorectal neoplasms (p-values>0.05). Additionally, sensitivity analyses excluding four participants reporting to have had any cancer diagnosis in the past in self-administrated questionnaires were also conducted, and yielded almost identical results.

tistically significant. For three markers (AREG, IL-6 and GDF-15) the 0.632+ adjusted AUCs for early tumor stage CRC were higher than 0.70 (i.e., 0.76, 0.74, and 0.72,

TABLE 3

Stage specific performance of specific protein markers for detection of CRC

| Marker | Tumor stages I and II | | Tumor stages III and IV | | |
|---|---|---|---|---|---|
| | Apparent AUC [95% CI] | .632+ AUC [95% CI] | Apparent AUC [95% CI] | .632+ AUC [95% CI] | p-value[a] |
| AREG | 0.79[0.67-0.91] | 0.76[0.61-0.95] | 0.65[0.50-0.80] | 0.60[0.39-0.87] | 0.168 |
| IL-6 | 0.78[0.67-0.90] | 0.74[0.62-0.94] | 0.60[0.45-0.75] | 0.49[0.23-0.77] | 0.064 |
| GDF-15 | 0.78[0.67-0.89] | 0.72[0.61-0.91] | 0.67[0.52-0.82] | 0.61[0.40-0.87] | 0.270 |
| HGF-receptor | 0.70[0.55-0.85] | 0.65[0.44-0.91] | 0.62[0.48-0.75] | 0.54[0.40-0.78] | 0.411 |
| CXCL9 | 0.70[0.55-0.85] | 0.64[0.46-0.89] | 0.61[0.47-0.76] | 0.48[0.24-0.75] | 0.421 |
| ErbB4-Her4 | 0.70[0.56-0.83] | 0.63[0.50-0.88] | 0.61[0.46-0.75] | 0.51[0.25-0.78] | 0.385 |
| CXCL10 | 0.70[0.55-0.84] | 0.62[0.45-0.88] | 0.62[0.47-0.76] | 0.49[0.23-0.77] | 0.445 |
| Flt3L | 0.69[0.55-0.83] | 0.62[0.45-0.88] | 0.59[0.43-0.74] | 0.50[0.26-0.76] | 0.320 |
| VEGFR-2 | 0.67[0.51-0.83] | 0.61[0.37-0.91] | 0.59[0.44-0.75] | 0.49[0.25-0.77] | 0.505 |
| CD69 | 0.66[0.50-0.82] | 0.60[0.41-0.90] | 0.59[0.44-0.75] | 0.51[0.25-0.78] | 0.546 |
| CXCL5 | 0.64[0.48-0.81] | 0.58[0.29-0.85] | 0.63[0.49-0.78] | 0.55[0.30-0.82] | 0.937 |
| CEA | 0.68[0.54-0.82] | 0.58[0.28-0.87] | 0.79[0.66-0.92] | 0.75[0.60-0.95] | 0.252 |
| PSA | 0.63[0.46-0.80] | 0.58[0.27-0.85] | 0.63[0.47-0.78] | 0.56[0.26-0.81] | 0.976 |
| EMMPRIN | 0.64[0.48-0.80] | 0.55[0.26-0.83] | 0.63[0.48-0.77] | 0.55[0.37-0.81] | 0.898 |
| Cathepsin-D | 0.65[0.50-0.80] | 0.54[0.21-0.83] | 0.61[0.46-0.75] | 0.49[0.24-0.75] | 0.688 |
| Caspase-3 | 0.62[0.47-0.78] | 0.52[0.28-0.82] | 0.63[0.48-0.79] | 0.55[0.27-0.85] | 0.923 |
| TNF-alpha | 0.59[0.43-0.74] | 0.48[0.22-0.76] | 0.67[0.51-0.82] | 0.60[0.37-0.88] | 0.480 |

[a]Delong test was employed to test the differences of AUCs between CRC at early stage and advanced stage.
Abbreviations: AUC, area under the receiver operating characteristic curve; CI, confidence interval.

Among these 17 protein markers, 9 protein markers were over-expressed and 8 protein markers showed lower levels in CRC cases compared with controls (Table 2). The 0.632+ adjusted AUCs of these 17 markers ranged from 0.70 to 0.55. Four markers, including AREG, CEA, GDF-15 and interleukin 6 (IL-6), yielded substantially better diagnostic performances than the others, with 0.632+ adjusted AUCs no less than 0.65. When the cutoff values were set to yield 80% specificity, the highest 0.632+ adjusted sensitivity was observed for CEA (52%). With cut-off values set to yield 90% specificity, the highest 0.632+ adjusted sensitivity was observed for AREG (36%).

Figure 2:
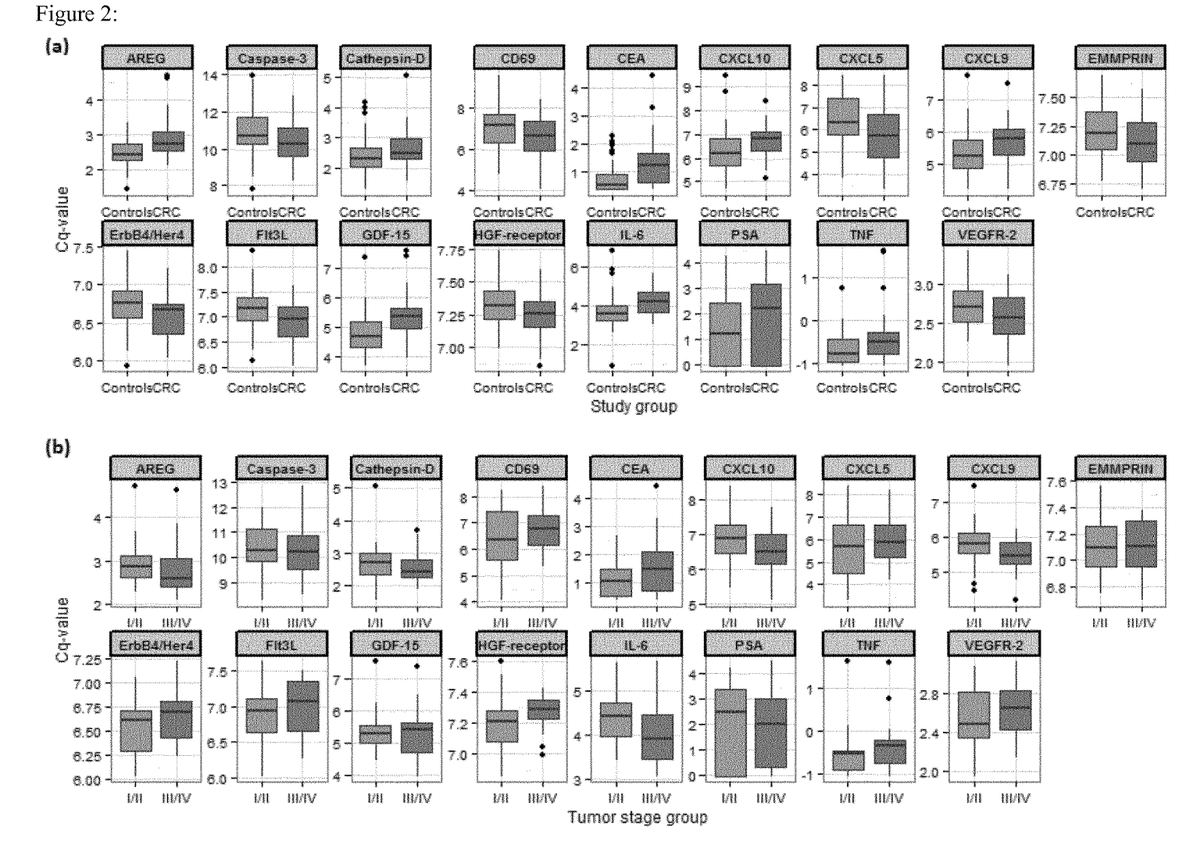
FIG. 2: Box plots of plasma levels for 17 protein biomarkers: (a) between CRC cases and controls; (b) early stages (I/II) and advanced stage (III/IV) CRC. The bottom and top of the box indicate the first (Q1) and third (Q3) quartiles, and the middle line in the box is the median; the upper-limit equals Q3 plus 1.5 times interquartile range (IQR), and the lower-limit equals Q1 minus 1.5 times IQR.

FIG. 2 shows the distribution of plasma levels for the 17 protein markers for CRC patients in early tumor stages and advanced tumor stages. 7 protein markers (IL-6, CXCL9, CXCL10, PSA, cathepsin-D, caspase-3 and AREG) showed higher levels in early tumor stages than in advanced ones. However, only the result for IL-6 was statistically significant (p-value<0.05). Table 3 shows the comparison of ROC analysis for these 17 markers between CRC patients at early and advanced stages. Most markers (13/17) showed higher adjusted AUCs in CRC patients at early tumor stages than at advanced ones. However, none of the differences was statistically significant. For three markers (AREG, IL-6 and GDF-15) the 0.632+ adjusted AUCs for early tumor stage CRC were higher than 0.70 (i.e., 0.76, 0.74, and 0.72, respectively). By contrast, CEA showed the highest 0.632+ adjusted AUC for advanced stage CRC (0.75).

Example 2: Development of a Colorectal Cancer Diagnostic Panel of 8 Biomarkers

The inventors used the Lasso Logistic regression model to construct a multi-marker prediction algorithm based on all 92 protein biomarkers. The following 8 markers were selected for inclusion in the algorithm: IFN-gamma, EMMPRIN, ErbB4-Her4, PSA, CD69, AREG, HGF-receptor and CEA (algorithm is shown in Table 4). The apparent AUC was 0.88 (95% CI, 0.81-0.95). Through the "0.632+ bootstrap subsampling approach", the adjusted AUC of this algorithm was 0.77 (95% CI, 0.59-0.91). Of note, this algorithm showed a similar diagnostic value for early stage CRC and advanced stage CRC (0.632+ adjusted AUC: 0.79 versus 0.75, respectively).

TABLE 4

Eight-marker algorithm derived through the Lasso logistic regression model: intercept and marker coefficients

| Variable | Intercept | INFγ | EMM-PRIN | ErbB4-Her4 | PSA | CD69 | AREG | HGFR | CEA |
|---|---|---|---|---|---|---|---|---|---|
| Coeff. | 7.57 | 0.0259 | −0.0887 | −0.8138 | 0.0642 | −0.1793 | 0.9605 | −0.5173 | 0.4450 |

Figure 3:
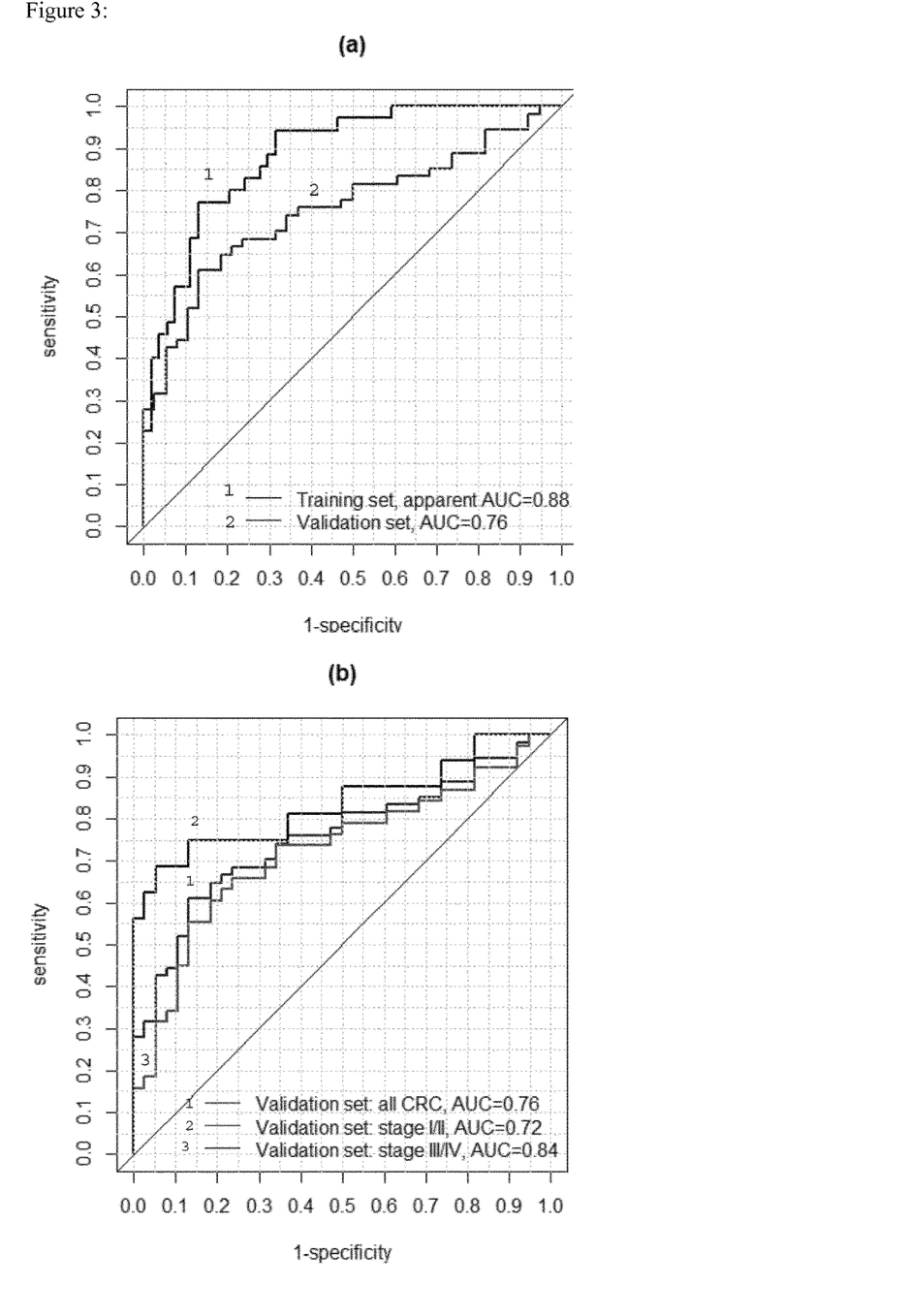
FIG. 3: Comparison of receiver operating characteristic curve for the eight-marker algorithm: (a) between the training set and the independent validation set; (b) between different subgroups in the independent validation set (i.e., all CRC cases, tumor stage I/II and tumor stage III/IV).

Finally, the inventors also validated this eight-marker algorithm in the independent validation set, which included 54 CRC cases and 38 controls free of colorectal neoplasms. The age distribution of this validation set was similar to the sage distribution in the main study from the screening setting, even though both cases and controls included somewhat lower proportions of men. The tumor stage distribution of cases in the independent validation set was similar to the stage distribution of CRC cases detected at screening colonoscopy according to the German screening colonoscopy registry. Table 5 and FIG. 3 show the diagnostic performance of the eight-marker algorithm for CRC prediction in the independent validation set. The AUC was 0.76 (95% CI, 0.65-0.85), and sensitivities at cutoffs yielding 80% and 90% specificities were 65% (95% CI, 41-80%) and 44% (95% CI, 24-72%), respectively. In this independent validation set, diagnostic performance was better for advanced stage than for early stage disease (AUC: 0.84 versus 0.72, respectively).

TABLE 5

The diagnostic performance of the eight-marker algorithm for CRC detection in an independent validation set

| CRC group | AUC [95% CI] | Sensitivity [95% CI] | |
| --- | --- | --- | --- |
| | | at 80% specificity | at 90% specificity |
| All CRC cases | 0.76 [0.65-0.85] | 65% [41-80%] | 44% [24-72%] |
| CRC at Stage I/II | 0.72 [0.60-0.84] | 61% [34-79%] | 34% [13-68%] |
| CRC at Stage III/IV | 0.84 [0.68-0.96] | 75% [50-94%] | 69% [44-94%] |

Abbreviations: AUC, area under the receiver operating characteristic curve; CI, confidence interval.

Figure 4:
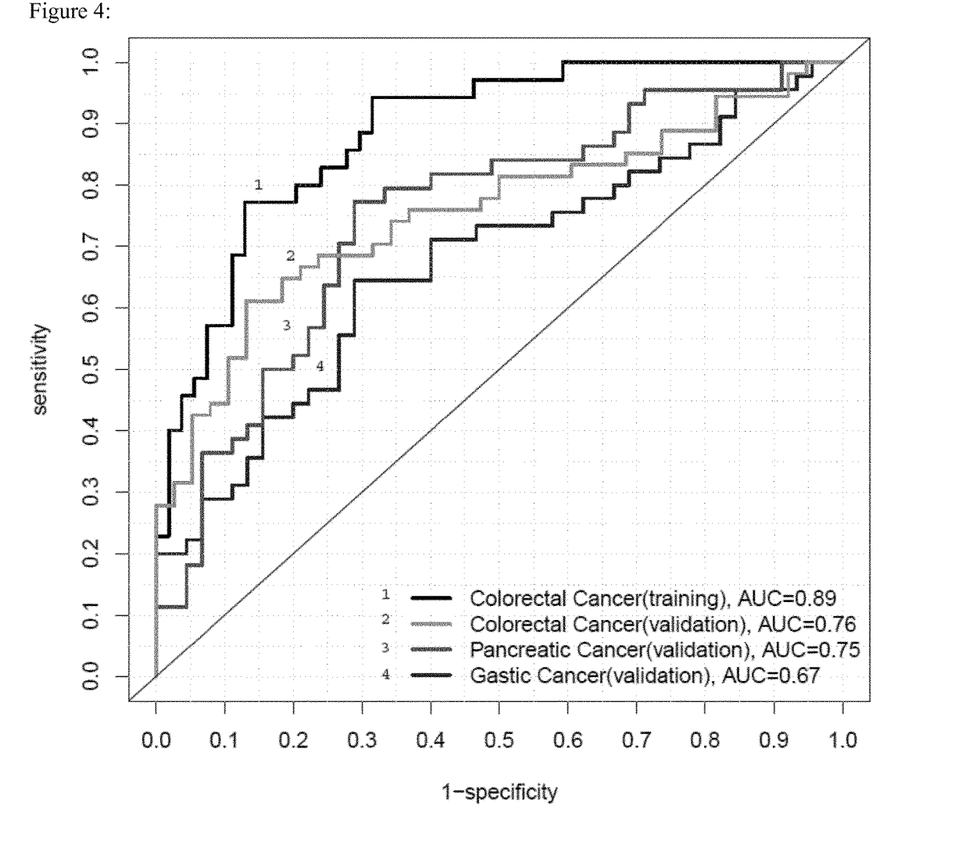
FIG. 4: Comparison of receiver operating characteristic curve for the eight-marker algorithm between the colorectal cancer training set, the colorectal cancer independent validation set, the gastric cancer set and the pancreatic cancer set.

Example 3: Validation of the Diagnostic Panel of 8 Biomarkers in the Diagnosis of qGastric Cancer and Pancreatic Cancer The diagnostic value of the 8 biomarker panel of the invention could also be validated for both pancreatic cancer and gastric cancer (FIG. 4), indicating the general applicability of the 8 biomarker panel for the diagnosis of cancers, not only colorectal cancer.

The invention claimed is:

1. An in vitro method for the diagnosis, prognosis, stratification and/or monitoring of colorectal cancer in a human subject, comprising the steps of:
   a) Providing a blood or plasma sample from the human subject,
   b) Detecting the level of AREG, CEA, HGF-receptor, ErbB4-Her4, CD69, PSA, EMMPRIN, and INF-gamma biomarkers in the blood or plasma sample,
   wherein a higher level of the biomarkers in the blood or plasma sample from the human subject as determined in step (b) compared to a healthy control or a reference value is indicative for the presence of colorectal cancer in the human subject.

2. The method according to claim 1, wherein the biomarkers are protein biomarkers.

3. The method according to claim 1, wherein the method is a screening method for establishing a first diagnosis of colorectal cancer in the human subject.

4. The method according to claim 1 wherein the biomarkers are detected using one or more antibodies.

5. The method of claim 4, wherein the biomarkers are detected by western blot, ELISA, Proximity Extension Assay, or mass-spectrometrically.

* * * * *